United States Patent [19]
Watanabe et al.

[11] Patent Number: 5,847,193
[45] Date of Patent: Dec. 8, 1998

[54] LABELLED COMPOUND

[76] Inventors: Yasuyoshi Watanabe, 5-20-19 Onohara-higashi, Minoo-shi, Osaka; Hironori Omura, 2-179-2 Minamimatsunaga-cho, Fukuyama-shi, Hiroshima; Yuji Furuya, 20-9 Jyusangenya Kannabe-cho, Fukayasu-gun, Hiroshima, all of Japan; Bengt Langström; Gunnar Antoni, both of c/o Uppsala University, PET-Centre, S-751 85 Uppsala, Sweden

[21] Appl. No.: 620,320

[22] Filed: Mar. 22, 1996

[30] Foreign Application Priority Data

Mar. 24, 1995 [JP] Japan ..................................... 7-066586
Oct. 12, 1995 [JP] Japan ..................................... 7-264015

[51] Int. Cl.$^6$ ....................... C07C 255/11; C07C 255/27; C12P 13/04
[52] U.S. Cl. ............................. 558/441; 435/106
[58] Field of Search ............................. 435/106; 558/441, 558/440

[56] References Cited

PUBLICATIONS

G. Antoni et al., *Eleventh International Symposium on Radiopharmaceutical Chemistry*, Abstracts, pp. 182–183 (1995).

Chem ABS 104: 1493682 Rohm et al J. Labelled Compd. Radiopharm 1985 22(9) 909–15.

Chem ABS 116: 55130m Willhardt et al DD291,579 Jul. 4, 1991.

Chem ABS 71:98987 & Ressler et al Biochem Biophy Acta 184(3) 578–82 (1969).

Chem ABS 116: 124278e Hermann et al "Enzymes Depend." Proce Int Symp. Vitam B6 Carbonyl Catal 8$^{th}$ 1990, 649–56.

*Primary Examiner*—Herbert J. Lilling
*Attorney, Agent, or Firm*—Wenderoth, Lind & Ponack

[57] ABSTRACT

The present invention provides a labelled β-cyano-L-alanine and a γ-cyano-α-aminobutyric acid, of which cyano group carbon is labelled with radionuclide $^{11}$C or $^{14}$C, or stable isotope $^{13}$C. The present invention also provides a labelled amino acids such as asparagine, asparatic acid, DABA, GABA, glutamine and glutamic acid synthesized by using the labelled β-cyano-L-alanine and the γ-cyano-α-aminobutyric acid as an intermediate. The labelled amino acids are useful for in vivo imaging of tumors and brain functions.

1 Claim, 12 Drawing Sheets

SDS-PAGE

1: Marker protein
2: GCABA synthase

○ Molecular weight marker
● GCABA synthase

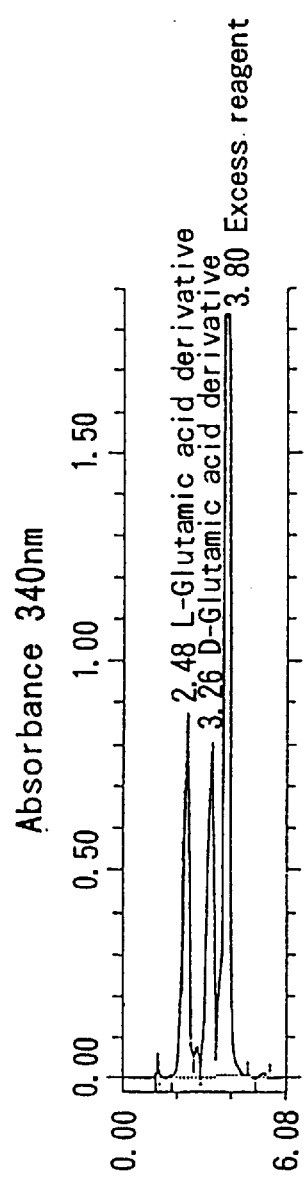
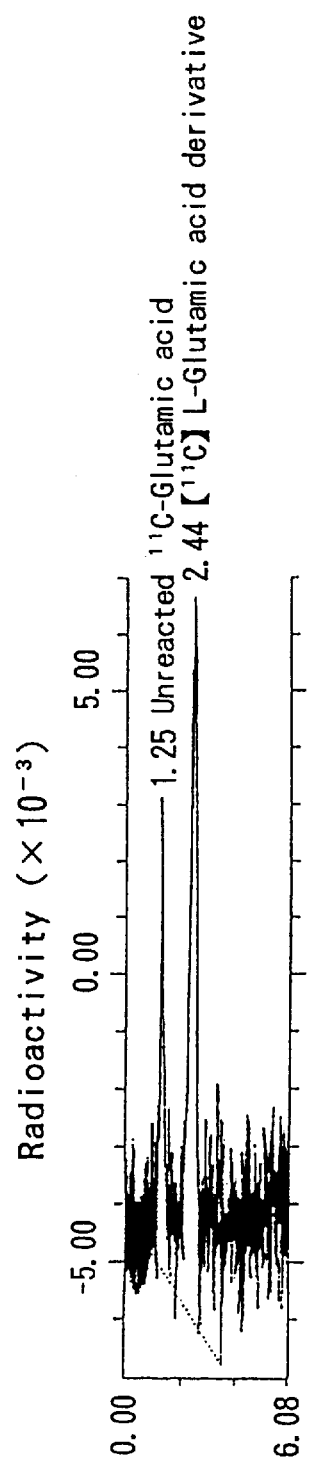

LABELLED COMPOUND

FIELD OF THE INVENTION

The present invention relates to a labelled compound and a method for manufacturing the compound. More particularly, the present invention relates to a compound labelled with radionuclide such as positron nuclide or stable isotope. The labelled compound of the invention is useful for imaging tumors and brain.

PRIOR ART

Physiological, pharmacological or biochemical processes of extra-trace substances have conventionally been traced in vivo by using various labelled compounds in many methods.

As one of the methods using such labelled compounds, Positron Emission Tomography (PET) method is now attracting the general attention, which consists of synthesizing a positron-labelled compound using a positron decay nuclide prepared in a cyclotron, administrating the compound into body and imaging the compound's behavior by means of PET. The positron nuclide can label various metabolites or drugs without causing any change in the structure thereof, because it mainly comprises elements constituting an organism such as carbon, nitrogen and oxygen. In addition, because of the characteristics of the released annihilation radiation, the PET permits measurement of the physiological, pharmacological and biochemical processes of extra-trace substances in vivo at a very high sensitivity and a very low concentration, thus providing information very useful for clinical purposes. An example is the diagnosis of tumor by means of PET using positron nuclide. It is generally believed that glycometabolism, amino acid metabolism, fat metabolism and nucleic acid metabolism exasperate more in tumor cells than in normal ones. Since these metabolisms in tumor directly represent viability of tumor and the status of proliferation thereof, trials have been made to diagnose tumor by using a compound available by labelling sugar or amino acid with positron nuclide.

Under these circumstances, $^{11}$C-L-methionine is now popularly employed for positron diagnosis of tumor. Currently, 2,4-Diaminobutyric acid (DABA), L-glutamine and L-glutamic acid are expected to serve as specific tumor markers. These amino acids are found to be incorporated into human or rat gliomacyte, and because of the preferential antitumor activity, they are further expected, not only as tumor markers, but also as new therapeutic drugs.

Actually, however, a labelled compound used in the PET method should have a short half-life of positron nuclide (for example, 20.4 minutes for $^{11}$C), and for clinical purposes, purity, specific radioactivity and ultimate quantity of radiation must satisfy clinical requirements. It is however very difficult to manufacture a positron-labelled compound which satisfies these requirements. Exposure of the operator during synthesis of the labelled compound is another problem. As a labelling method permitting rapid operation and giving a high radiochemical yield sufficient to meet practical requirements has not as yet been established, progress of the PET method has not been satisfactory in terms of application for biological observation and diagnosis, for example, imaging of tumor or brain.

For DABA, asparagine, aspartic acid, L-glutamine and L-glutamic acid, expected because of the favorable characteristics, for example, positron labelling has been very difficult for these reasons.

As to the difficulty of labelling, this is also the case with labelling with β-decay nuclide or other radioactive isotope, or further, with a stable isotope, in addition to the case with positron nuclide.

SUMMARY OF THE INVENTION

The present invention has an object to provide a novel compound labelled with radionuclide or stable isotope which is achievable as a rapid labelling giving a high radiochemical yield, and a labelled compound which is a synthetic intermediate thereof.

The other object of the invention is to provide a method for manufacturing the labelled compounds.

A first invention provided by the present invention covers β-cyano-L-alanine, a salt thereof or a derivative thereof having protecting group, of which cyano group carbon is labelled with radionuclide or stable isotope.

A second invention is a method for manufacturing the labelled compound of the first invention, which comprises reacting an amino acid expressed by the following Formula (1), a salt thereof or a derivative thereof having protecting group with a cyanic compound of which cyano group is labelled with radionuclide or stable isotope in the presence of a thermostable β-cyano-L-alanine synthase:

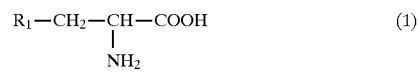

(where, $R_1$ is hydrogen atom, halogen atom, a hydrocarbon group, an oxygen-containing group or a sulfur-containing group).

A third invention of the present invention covers a labelled compound which is an amino acid expressed by the following formula (2), a salt thereof or a derivative thereof having protecting group:

(where, $R_2$ represents —*$CONH_2$ (asparagine), —*COOH (asparatic acid), —*$CH_2$—$NH_2$ (DABA), and *C is carbon labelled with radionuclide or stable isotope).

A fourth invention of the present invention covers a method for manufacturing the labelled compound of the third invention, which comprises organically or enzymatically synthesizing the amino acid, the salt thereof or the derivative thereof having protecting group by using, as an intermediate, the labelled compound of the first invention or a labelled compound manufactured by the method of the second invention.

Further, a fifth invention provided by the present invention covers a labelled compound which is γ-cyano-α-aminobutyric acid, a salt thereof or a derivative thereof having protecting group, of which cyano group carbon is labelled with radionuclide or stable isotope.

A sixth invention covers a method for manufacturing the labelled compound of the fifth invention, which comprises reacting an amino acid expressed by the following Formula (3), a salt thereof or a derivative thereof having protecting group with a cyanic compound of which cyano group is labelled with radionuclide or stable isotope in the presence of a thermostable γ-cyano-α-aminobutyric acid synthase:

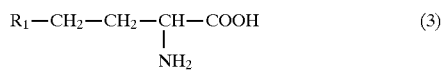

(where, $R_1$ is hydrogen atom, halogen atom, a hydrocarbon group, an oxygen-containing group or a sulfur-containing group).

A seventh invention covers a labelled compound which is an amino acid expressed by the following formula (4), a salt thereof or a derivative thereof having protecting group:

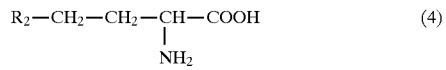

(where, $R_2$ represents $-*CONH_2$ (glutamine), or $-*COOH$ (glutamic acid), and $*C$ is carbon labelled with radionuclide or stable isotope).

An eighth invention covers a method for manufacturing the labelled compound of the seventh invention, which comprises organically or enzymatically synthesizing the amino acid, the salt thereof or the derivative thereof having protecting group by using, as an intermediate, the labelled compound of the fifth invention or a labelled compound manufactured by the method of the sixth invention.

BRIEF DESCRIPTION OF THE DRAWINGS

FIGS. 17(a)–17(b) are the result of HPLC analysis showing that the $^{11}C$-labelled glutamic acid of Example 7 is L-form.

DETAILED DESCRIPTION OF THE INVENTION

Figure 1:
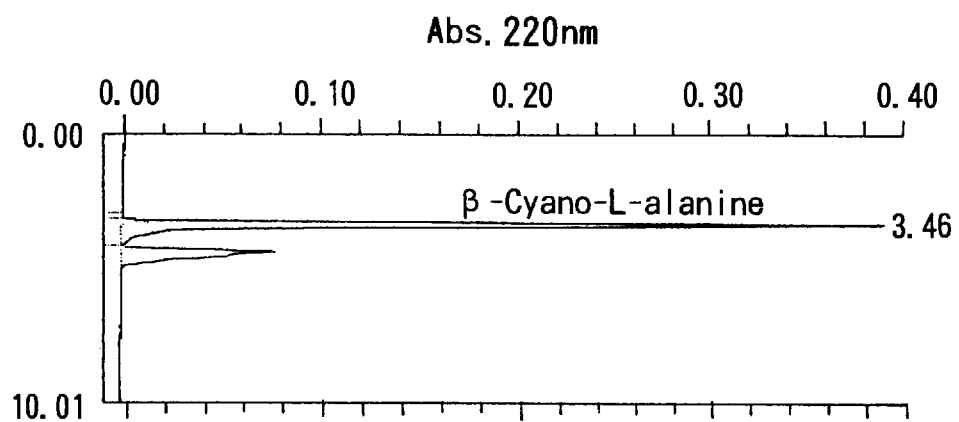
FIG. 1 is the result of HPLC analysis showing that the reaction product of Example 2 is β-cyanic alanine.

Both the labelled β-cyano-alanine or a salt thereof or a protective derivative thereof which is covered by the first invention (hereinafter referred to as the "labelled β-cyano-L-alanine compound") and the labelled γ-cyano-α-aminobutyric acid or a salt thereof or a protected derivative thereof which is covered by the fifth invention (hereinafter referred to as the "labelled γ-cyano-α-aminobutyric acid compound") are novel compounds provided by the present invention. These compounds can be expressed, for example by the following Formula (5) (labelled β-cyano-L-alanine compound) or the Formula (6) (labelled γ-cyano-α-aminobutyric acid compound):

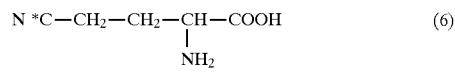

These compounds as shown in the Formulae (5) and (6) are characterized in that cyano group carbon atom ($*C$) is labelled with radionuclide or stable isotope. The terms "radionuclide" and "stable isotope" using for labelling are denoted as having wide-range definitions including positron nuclide $^{11}C$, radioactive isotope $^{14}C$, and further, stable isotope $^{13}C$. What should be noted about these labels, particularly in the present invention, is that a compound labelled with positron nuclide $^{11}C$ is provided. This compound is very useful as a synthesis intermediate of a labelled amino acid compound manufactured through conversion of β-cyano group or γ-cyano group. Because of the possibility of administering in animal body, this labelled amino acid compound can be used in the application of the PET method.

Free amino group or carboxyl group may of course be present in the form of a salt of acid or alkali, or may be a derivative protected by a conventional amino acid, or by any of various protecting groups in peptide synthesis. All such cases are included in the labelled β-cyano-L-alanine compound and the labelled γ-cyano-α-aminobutyric acid compound of the present invention.

Now, the following paragraphs describe the methods for manufacturing the labelled β-cyano-L-alanine compound and the γ-cyano-α-aminobutyric acid compound, respectively, and the labelled amino acid compounds synthesized by using these labelled compounds as synthesis intermediates.

(1) Manufacture of labelled β-cyano-L-alanine compound:

The labelled β-cyano-L-alanine compound of the present invention can be manufactured by reacting an amino acid as expressed by the above-mentioned Formula (1) or a salt thereof or a protected derivative thereof, with a cyanic compound of which cyano group carbon is labelled with radionuclide or stable isotope, in the presence of β-cyano-L-alanine synthase. It is needless to mention that it can be manufactured through conventional chemical synthesis.

When manufacturing by the use of an enzyme, it is possible to use β-cyano-L-alanine synthase derived from a bacterium selected from the group consisting of, for example, Acinetobacter, Aerobacter, Agrobacterium, Arthrobacter, Bacillus, Brevibacterium, Cellulomanas, Corynebacterium, Enterobacter, Erwinia, Escherichia, Flavobacterium, Hafnia, Micrococcus, Mycobacterium, Nocardia, Pseudomonas, Rhodococcus, Salmonella, Serratia, and Staphylococcus. These bacteria can more specifically be shown in Table 1.

TABLE 1

Specific activity for β-Cyanoalanine synthase in bacterial AKU stock culture.

| | | | Specific activity ($\times 10^3$ U/mg dry cell mass) | | | | | |
|---|---|---|---|---|---|---|---|---|
| AKUNo. | Strain | | Ser | O-M-Ser | Cys | O-P-Ser | B-Cl-Ala | O-A-Ser |
| 8 | Escherichia coll K12 | | 7.35 | 0.56 | 1.48 | 17.3 | 8.3 | 10.7 |
| 23 | Aerobecter aerogenes K-6 | | | 0.14 | 0.42 | | 4.41 | 5.8 |
| 29 | Enterobacter aerogenes | IFO 12010 | | | 0.53 | | 12.1 | 11.7 |
| 41 | Erwinis carotovora subsp. | IFO 12380 | | 0.87 | 0.11 | | | |
| 45 | Escherichia coll K12 | IFO3301 | 6.21 | | 2.73 | 3.87 | 13 | |
| 62 | Serratia plymuthicum | IFO 3055 | | | | | 1.48 | |
| 95 | Salmonella typhimurium | IFO 13245 | | 1.79 | 0.93 | | 11.7 | 11.3 |
| 147 | Flavobacterium arborescens | IFO 3750 | | | 0.41 | | | |
| 157 | Flavobacterium autothermophilum | | | 0.43 | | | | |
| 238 | Bacillus thuringiansis | IFO 3951 | | | | 0.11 | | |
| 245 | Bacillus cereus | IAM 1029 | 8.48 | | 0.23 | 0.38 | | |
| 300 | Agrobacterium lumefaciens | IAM B-26-1 | 0.29 | | | 0.1 | 3.83 | 3.24 |
| 314 | Agrobacterium lumefaciens | IFO 119264 | | | 0.28 | | | 0.23 |
| 501 | Micrococcus luteus | IFO 3333 | 0.04 | | | | | 1.52 |
| 502 | Micrococcus flavus | IFO 3242 | | | | | | 0.33 |
| 504 | Micrococcus luteus | IFO 3763 | 31.4 | | | 0.04 | | 0.78 |
| 506 | Micrococcus roseus | IFO 3788 | 0.49 | | 0.36 | 0.05 | 2.32 | |
| 524 | Staphylococcus lureus | IFO 3762 | 3.33 | | 0.39 | 0.39 | | |
| 540 | Micrococcus luteus | IFO 3064 | 7.88 | 0.23 | | 0.15 | | |
| 602 | Corynebacterium equl | IAM 1038 | 1.77 | | | 0.15 | | |
| 604 | Corynebacterium aqualicum | IFO 12154 | | | | | 1.83 | 10.5 |
| 605 | Corynebacterium paurometabolum | IFO 12160 | | | | 0.06 | | 1.28 |
| 626 | Arthrobacter simplex | IFO 12069 | | | | | 7.67 | 2.78 |
| 635 | Arthrobacter sulfureus | IFO 12678 | | 0.11 | | | | 1.31 |
| 637 | Arthrobacter alrocyaneus | IFO 12956 | 1.93 | | | | | |
| 641 | Bravibacterium ammonlagenes | IFO 12071 | | | | | 9.08 | 3.57 |
| 643 | Bravibacterium P145 | | 0.2 | | | | 2.12 | 0.55 |
| 647 | Bravibacterium protophormiae | IFO 12126 | 0.46 | | | | | 1.33 |
| 648 | Bravibacterium linens | IFO 12141 | 6.45 | | 0.77 | 0.53 | | |
| 655 | Bravibacterium stationis | IFO 12144 | | | 0.23 | | 2.44 | |
| 671 | Cellulomonas firml | IAM 12107 | | | | | 1.93 | 1.52 |
| 672 | Cellulomonas sp. NT3060 | | | | 0.31 | | | |
| 700 | Halnia alvei | IFO 3731 | 0.17 | | | | 33.5 | 5.84 |
| 720 | Aci netobacter cnicoacelicus | IFO 12552 | 25.7 | 0.64 | 1.13 | 0.8 | | |
| 802 | Pseudomonas Imgl | IFO 3458 | 37.7 | 0.5 | | 0.66 | | 9.59 |
| 803 | Pseudomonas riboflavin | IFO 3140 | | 0.43 | 0.37 | | | 0.69 |
| 804 | Pseudomonas aeruginosa | IFO 3918 | 9.57 | | | 11.5 | | |
| 806 | Pseudomonas solanacearum | IFO 3509 | | 0.29 | 0.32 | | | |
| 806 | Pseudomonas taetrolens | | 1.7 | | | | 9.01 | 19.7 |
| 810 | Pseudomonas sp. | | 3.67 | 0.5 | 0.48 | 0.32 | | |
| 820 | Pseudomonas ovalls No. 111 | | 90.2 | | | | 8.61 | 41.5 |
| 838 | Pseudomonas aureofaclens | IFO 3521 | 12.7 | | | | | |
| 839 | Pseudomonas diminuta | IFO 12699 | | | 0.25 | 0.11 | | |
| 844 | Pseudomonas syncyanea | IFO 3757 | 3.64 | | | | | |
| 846 | Pseudomonas synxantha | IFO 3906 | | | 0.27 | | | |

Ser - L-serine
O-M-Ser - O-methyl-L-serine
Cys - L-cysteine
O-P-Ser - O-phosphoryl-L-serine
β-Cl-ALa - β-chloro-L-alanine
O-A-Ser - O-scetyl-L-serine In the manufacturing method of the present invention, it is preferable to use a β-cyano-L-alanine synthase derived from a bacterium of Bacillus, or more specifically, an enzyme isolated from, for example, *Bacillus stearothermophilus*. Particularly, *Bacillus stearothermophilus* CN3 is the most preferable for the present invefntion. This strain was isolatede by the present inventors from a natural source and deposited on Aug. 8, 1994 to National Institute of Bioscience and Human Technology under a deposit number of FERM BP-4773.

Actually, as a synthase from these bacteria, a thermostable β-cyano-L-alanine synthase having the following properties can be presented:

(1) action: generating β-cyano-L-alanine from O-acetyl-L-serine and a cyanic compound;
(2) optimum pH: 7.0 to 9.0;
(3) stable pH: 6.0 to 10.0;
(4) optimum temperature: 40° to 50° C.
(5) thermostability: stable up to 70° C. when holding at pH 7.5 for 30 minutes;
(6) molecular weight: 60,000 to 80,000 with gel filtration.

This enzyme is manufacturable by culturing a thermophilic Bacillus on a β-cyano-L-alanine synthase producing medium, and then isolating the target β-cyano-L-alanine synthase from the cultured bacterium. In this process, the CN3 strain would be used preferably. This enzyme requires, for example, pyridoxal phosphate as a coenzyme, and applicable substrates include O-acetyl-L-serine, L-cystine, L-serine, O-methyl-L-serine, O-phosphoryl-L-serine, O-succinyl-L-serine and β-chloro-L-alanine.

In the reaction of the compound of Formula (1) using the synthase above, the substituent of the Formula (1) compound may more specifically be —O-alkyl group, —O-phosphoryl group, or halogen atom, and the cyanic compound may be prussic acid (CN⁻), NaCN or KCN of which carbon is labelled.

The labelled cyanic compound is available, in the case of prussic acid labelled with positron nuclide $^{11}$C, by for example reducing $^{11}$CO$_2$ prepared in a cyclotron into $^{11}$CH$_4$, and reacting it with ammonia in the presence of platinum (Pt) catalyst at a high temperature of about 1,000° C., just as in the ordinary prussic acid synthesis. The β-cyano-L-alanine compound of which cyano group carbon is labelled with positron nuclide $^{11}$C can be manufactured by reacting this cyanic compound with the Formula (1) amino acid in an aqueous medium in the presence of the synthase above. Similarly, β-cyano-L-alanine compounds labelled with $^{13}$C and $^{14}$C are produced.

(2) Manufacture of labelled γ-cyano-α-aminobutyric acid compound:

The labelled γ-cyano-α-aminobutyric acid compound of the present invention can be manufactured by by reacting an amino acid as expressed by the above-mentioned Formula (3) or a salt thereof or a protected derivative thereof, with a cyanic compound of which cyano group carbon is labelled with radionuclide or stable isotope, in the presence of γ-cyano-α-aminobutyric acid synthase. It is of course manufacturable also through chemical synthesis.

The thermostable γ-cyano-α-aminobutyric acid synthase, when manufacturing by the use of an enzyme, may be one available by isolating from a thermophilic Bacillus, or more specifically, for example, may be one obtained from *Bacillus stearothermophilus* CN3 strain (FERM BP-4773).

Actually, a thermostable γ-cyano-α-aminobutyric acid synthase having the following properties may be presented as an example of the enzyme for the above-mentioned reaction:

(1) action: producing γ-cyano-α-aminobutyric acid from O-acetyl-L-homoserine and cyanic compoppund;
(2) optimum pH: 7.5 to 8.5;
(3) stable pH: 6.0 to 10.5;
(4) optimum temperature: 55° to 65° C.;
(5) thermostability: stable up to 65° C. when holding at pH of 7.5 for 30 minutes;
(6) molecular weight: about 180,000 with gel filtration.

This enzyme can be manufactured, for example, by culturing *Bacillus stearothermophilus* CN3 strain on a γ-cyano-α-aminobutyric acid synthase producing medium, and then, isolating the target enzyme. This enzyme requires, for example, pyridoxal phosphate as a coenzyme, and applicable substrates include O-acetyl-L-homoserine, or L-homocystine.

For example, in the reaction of the Formula (3) compound using the synthase above, the substituent R1 of this Formula (3) compound may more specifically be —O-acyl group, —O-alkyl group, —O-phosphoryl group, or halogen atom, and the cyanic compound be prussic acid (CN⁻), NaCN or KCN of which carbon is labelled. In the case of prussic acid labelled with positron nuclide $^{11}$C, the labelled cyanic compound can be obtained by reducing $^{11}$CO$_2$ prepared in a cyclotron into $^{11}$CH$_4$, and reacting it with ammonia at a high temperature of about 1,000° C. in the presence of a platinum (Pt) catalyst, just as in the ordinary prussic acid synthesis. The γ-cyano-α-aminobutyric acid compound of which cyano group carbon is labelled with positron nuclide $^{11}$C can be manufactured by reacting this cyanic compound with the above-mentioned Formula (3) amino acid in the presence of said synthase. Similarly, there is available the γ-cyano-α-aminobutyric acid compound labelled with $^{13}$C or $^{4}$C.

(3) Manufacture of labelled amino acid:

The labelled amino acid compound of the present invention is manufacturable by using the above-mentioned labelled β-cyano-L-alanine compound or labelled γ-cyano-α-aminobutyric acid compound as the intermediate. In this case, for example, it is possible to convert cyano group into amino acid through a reduction reaction, and cyano group into amide acid or carboxyl group through a hydrolysis reaction. More specifically, the above-mentioned Formula (2) or (4) labelled amino acid is manufacturable by reduction or decomposition under various conditions, and further, the labelled amino acid compound or a salt thereof or a protected derivative thereof by the conventional method.

The reduction reaction is made possible by a method based on Raney nickel or Raney cobalt, or any of the various means including the conventional methods such as one using NaBH$_4$ or other reducing agent. This is also the case with the hydrolysis reaction. By the application of any of these means including the enzyme method, for example, the following labelled amino acids are synthesized from the labelled γ-cyano-L-alanine compound:

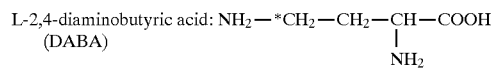

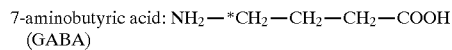

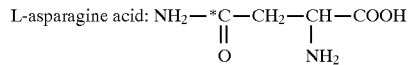

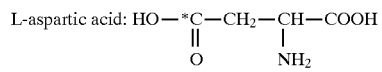

The following labelled amino acid compounds are for example manufactured from the labelled γ-cyano-α-aminobutyric acid compound:

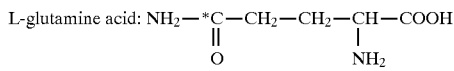

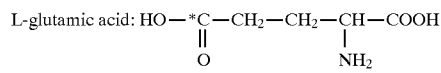

The labelled amino acid compound thus synthesized can be combined, for example, with a biopolymer such as peptide or protein through substitution of amino acid residue or addition of other amino acid residue.

The present invention permits, as described above, easy radiochemical labelling or stable isotope labelling with positron nuclide $^{11}$C or the like through substitution or addition reaction of the amino acid and a cyanic compound in the presence of a specific synthase. Particularly, the findings that bacteria of Bacillus can produce an enzyme for this reaction make it possible, in the present invention, to achieve labelling not only with positron nuclide $^{11}$, but also with a radioisotope such as $^{14}$C or a stable isotope such as $^{13}$C.

Labelling of various amino acids makes a great contribution to observation and diagnosis by the PET method as well as to NMR diagnosis and biochemical research on metabolism. Although a method of labelling amino group or carboxyl group of amino acid with an isotope has conventionally been known, these groups were easily metabolized in vivo, so that it was impossible to trace the mother nucleus of amino acid. The present invention makes it possible to label carbon which is hard to metabolize, and now permits very easy tracing of the mother nucleus. It is possible to label the mother nucleus with a β-decaying radioisotope $^3$H or $^{14}$C through chemical synthesis consuming a long period of time. However, because radiation does not run through the body when using these isotopes, the position of a labelled compound in vivo cannot be detected from outside the body. On the other hand, $^{11}$C nuclide, which β$^+$ decays and releases γ rays upon hitting negatrons inside cells and tissues, can be detected from outside the body and therefore permits tracing distribution and localization of a labelled compound administered in vivo from outside. As it is possible to trace behavior of the labelled compound in vivo while comparing between before and after treatment or with clinical effect, it is very useful for diagnosis and medical treatment of diseases.

The present invention will now be described in further detail by means of Examples.

EXAMPLE 1

A thermostable β-cyano-L-alanine synthase was prepared as follows.

A culture medium comprising 1% polypepton, 0.25% yeast extract, 0.1% glycerol, 0.1% $(NH_4)_2SO_4$, 0.05% $MgSO_4 \cdot 7H_2O$, and 0.1% $K_2HPO_4$ (pH: 7.2) was poured into two large test tubes by equal amounts of 8 ml, sterilized at 120° C. for 20 minutes, and cooled. Then, *Bacillus stearothermophilus* CN3 strain (No. FERM BP-4773) was inoculated in an amount of one platinum spoon, and after culture at 60° C. for 24 hours, the product was used as a basic medium. An antifoaming agent (made by Asahi Denka Company, ADEKANOL KG-126) in an amount of 0.01% (V/V) was added to a culture medium having the same composition as above. The resultant medium in an amount of 1.6 l was placed in a jar fermenter having a volume of 2 l, and after sterilization at 120° C. for 20 minutes and cooling, 16 ml of the above-mentioned basic medium (for two test tubes) were inoculated. Culture was thus conducted at 60° C. for 27 hours under stirring conditions including a volume of aeration of 1.6 l/minute and a stirring velocity of 300 rpm, and the resultant medium was used as the preculture medium. Then, a culture comprising 1% polypepton, 0.25% yeast extract, 0.1% glycerol, 0.1% $(NH_4)_2SO_4$, 0.05% $MgSO_4 \cdot 7H_2O$, 0.1% $K_2HPO_4$, and 0.1% L-serine (pH: 7.2) in an amount of 160 l was placed in a jar fermenter having a volume of 200 l, sterilized at 120° C. for 30 minutes, cooled, and then, 1.6 l of the above-mentioned preculture medium were inoculated to conduct culture at 60° C. for 24 hours under stirring conditions including a volume of aeration of 120 l/minute and a stirring velocity of 200 rpm. After culturing, bacteria were collected through sharpless centrifugal separation.

The resultant bacteria were equally divided into eight (each in an amount of 20 l), and were each suspended in an appropriate amount of potassium phosphate buffer solution (10 mM, pH: 8.0, containing 0.1 mM dithiothreitol) to subject to cryopreservation at −80° C. This was used for the subsequent manufacture of enzyme by defrosting.

An amount of 60 l of the frozen bacteria was suspended to give a total amount of about 2,000 ml, and the bacteria were crushed on a Dyno-mill (made by WAB company). The crushed solution was centrifugally separated to obtain 2,100 ml of cell-free extract by removing residual bacteria.

Ammonium sulfate was added to this cell-free extract to achieve 40% saturation. After holding for a night, precipitate was removed by centrifugal separation, and ammonium sulfate was added again to the resultant supernatant to achieve 90% saturation. The saturated supernatant was held for 5 hours and a precipitate was obtained by centrifugal separation. The precipitate thus obtained was dissolved in a 10 mM potassium phosphate buffer solution (pH: 8.0) containing 0.1 mM dithiothreitol, and was desalted with a buffer solution of the same composition by the use of a dialysis membrane. Ethanol previously cooled to −80° C. was added to the thus desalted solution in an amount of 1,065 ml to achieve an ultimate concentration of 70%, and a precipitate was obtained through centrifugal separation. The resultant precipitate was suspended in a 10 mM potassium phosphate buffer solution (pH: 8.0) containing 0.1 mM dithiothreitol and was subjected to a heat treatment at 70° C. for 30 minutes. After removing precipitate through centrifugal separation, the supernatant in an amount of 1,024 ml was passed through a DEAE-cellurofine A-500 column (6.0 cm diameter×18 cm length) previously equilibrated with a 10 mM potassium phosphate buffer solution (pH: 8.0) containing 0.1 mM dithiothreitol for adsorption of enzyme. After washing with a buffer solution having the same composition, the enzyme was eluted by gradient elution from the 10 mM potassium phosphate buffer solution (pH: 8.0) containing 0.1 mM dithiothreitol to a 100 mM potassium phosphate buffer solution (pH: 8.0) containing 0.1 mM dithiothreitol and 0.5M NaCl to collect an active fraction.

Ammonium sulfate was added to this active fraction so as to achieve 80% saturation, and after holding for a night, a precipitate was obtained through centrifugal separation. This precipitate was dissolved in a 10 mM potassium phosphate buffer solution (pH: 8.0) containing 0.1 mM dithiothreitol, and subjected to an adjusted electrophoresis (7.5% polyacrylamide gel). After electrophoresis, an active portion in the gel was cut out, milled, and an enzyme was extracted by means of a 10 mM potassium phosphate buffer solution (pH: 8.0) containing 0.1 mM dithiothreitol. Ammonium sulfate was added to this active fraction so as to achieve 30% saturation, passed through a Phenyl Sepharose CL-4B column (2.5 cm diameter×12 cm length) previously equilibrated with 30% saturated ammonium sulfate and a 10 mM potassium phosphate buffer solution (pH: 8.0) containing 0.1 mM dithiothreitol for adsorption of an enzyme. After washing with a buffer solution having the same composition, the enzyme was eluted by gradient elution from the 30% saturated ammonium sulfate and the 10 mM potassium phosphate buffer solution (pH: 8.0) containing 0.1 mM dithiothreitol to a 10 mM potassium phosphate buffer solution (pH: 8.0) containing 0.1 mM dithiothreitol to collect an active fraction. Ammonium sulfate was added to this active fraction so as to achieve 30% saturation, and the saturated fraction was passed through an Octyl Sepharose CL-4B column (1.5 cm diameter×10 cm length) previously equilibrated with 30% saturated ammonium sulfate and a 10 mM potassium phosphate buffer solution (pH: 8.0) containing 0.1 mM dithiothreitol, for adsorption of an enzyme. After washing with a buffer solution having the same composition, an active fraction was collected by eluting the enzyme by the gradient elution method from the 30% saturated ammonium sulfate and the 10 mM potassium phosphate buffer solution (pH: 8.0) containing 0.1 mM dithiothreitol to a 10 mM potassium phosphate buffer solution (pH: 8.0) containing 0.1 mM dithiothreitol. The enzyme preparation thus obtained was confirmed to be single in terms of electrophoresis.

For the process of acquiring enzyme as described above, enzyme activity, yield and the like of each step are shown in Table 2. The term "Unit" as used in Table 2 is defined as the enzyme activity of generating β-cyano-L-alanine in an amount of 1 μmol during one minute, as measured by the activity measuring method shown in Table 3.

TABLE 2

| Step | Total activity (units) | Total protein (mg) | Specific activity (units/mg) | Fold | Yield (%) |
|---|---|---|---|---|---|
| 1. Cell-free extract | 26500 | 43000 | 0.616 | 1.00 | 100 |
| 2. (NH$_4$)$_2$SO$_4$ 40–90% | 19500 | 22400 | 0.871 | 1.49 | 77.8 |
| 3. EtOH treatment | 14200 | 15300 | 0.928 | 2.01 | 71.7 |
| 4. Heat treatment | 7940 | 2660 | 2.99 | 7.87 | 48.7 |
| 5. DEAE-Cellurofine A-500 | 6460 | 619 | 10.4 | 16.9 | 24.4 |
| 6. Native PAGE | 3240 | 99.4 | 32.6 | 52.9 | 12.2 |
| 7. Phenyl Sepharose CL-4B | 2690 | 35.0 | 76.6 | 124 | 10.1 |
| 8. Octyl Sepharose CL-4B | 2420 | 18.1 | 134 | 218 | 9.14 |

(from 60 l of culture medium)

TABLE 3

| Reaction liquid composition | | concentration |
|---|---|---|
| 1M-potassium phosphate buffer solution (pH:7.5): | 10 μl | 50.00 mM |
| H$_2$O | 80 μl | |
| 0.8 mM pyridoxal phosphate: | 20 μl | 0.08 mM |
| 50 mM O-acetyl-L-serine: | 20 μl | 5.00 mM |
| 100 mM potassium cyanide: | 20 μl | 10.00 mM |
| Enzyme solution | 50 μl | |
| Total: | 200 μl | |

Reaction at 45° C. for 10 minutes
Holding at 100° C. for 2 min. (reaction discontinued)
Centrifugal separation at 15,000 rpm for 10 min.
Supernatant
Quantitative measurment of the synthesized β-cyano-L-alanine with HPLC.

The resultant enzyme, having β-cyano-L-alanine synthetic activity from O-acetyl-L-serine and cyanic compound, had the following properties:

(1) thermostability: stable at temperatures of up to 70° C. (20 mM potassium phosphate buffer solution, pH: 7.5, heat treatment for 30 minutes);

(2) optimum temperature: 45° C. (20 mM potassium phosphate buffer solution, pH: 7.5);

(3) pH stability: stable at pH 6 to 10 (20 mM buffer solution, treatment at 60° C. for 30 minutes);

(4) optimum pH: pH 8.0 (20 mM potassium phosphate buffer solution);

(5) molecular weight: 70,000 (gel filtration);

(6) subunit molecular weight: 34,000 (SDS-PAGE); and (7) number of subunits: 2.

EXAMPLE 2

H$^{11}$CN was prepared by reducing $^{11}$CO$_2$, having positron nuclide $^{11}$C prepared in cyclotron, at 400° C. in a mixed atmosphere of H$_2$ and N$_2$ in the presence of Ni into $^{11}$CH$_4$, and contact-reacting the resulting $^{11}$CH$_4$ with ammonia using platinum (Pt) as a catalyst at a temperature of 1,000° C. The resultant H$^{11}$CN in the form of a mixed gas was passed through a 50% H$_2$SO$_4$ solution in an amount of 1.5 ml to remove residual ammonia, further brought into contact with P$_2$O$_5$ to remove ammonia, and H$^{11}$CN was trapped with 50 mM KOH in an amount of 350 μl.

O-acetyl-L-serine was mixed, together with the β-cyano-L-alanine synthase obtained in Example 1, into this H$^{11}$CN aqueous solution, and was reacted at the room temperature.

The product was analyzed under the following conditions:

Column: Beckman C-18 Spherisorb (4.6×250 mm);
Eluent: 10 mM Potassium phosphate buffer (pH: 4.6);
Flowrate: 0.75 ml/min;
Detection: UV 220 nm and Radiodetector;
Temperature: Room temperature; and
Injection volume: 10–20 μl.

Figure 2:
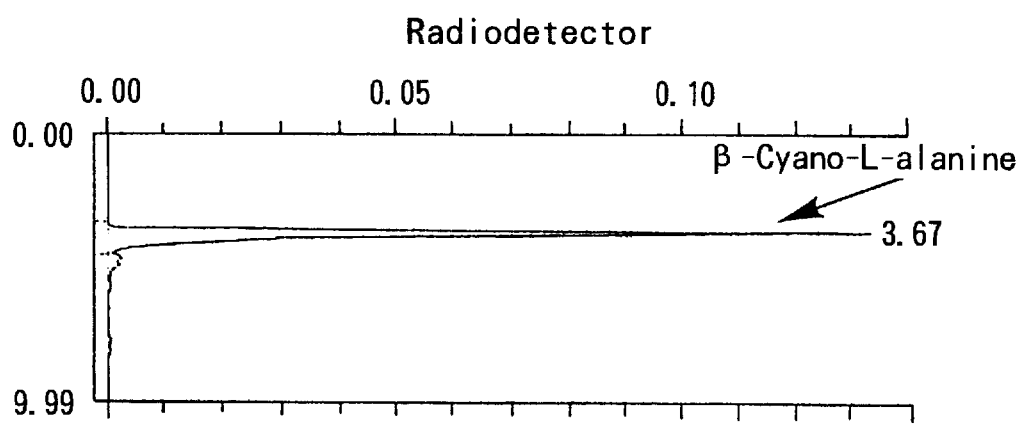
FIG. 2 is the result of HPLC analysis showing that the reaction product of Example 2 is β-cyanic alanine labelled with $^{11}C$.

The results of analysis with UV 220 nm and radiodetector are shown in FIGS. 1 and 2. It was confirmed from these results that the reaction product is β-cyano-L-alanine from the comparison with the retention time of standard, and the presence of cyano group having positron nuclide $^{11}$C was also confirmed.

Figure 3:
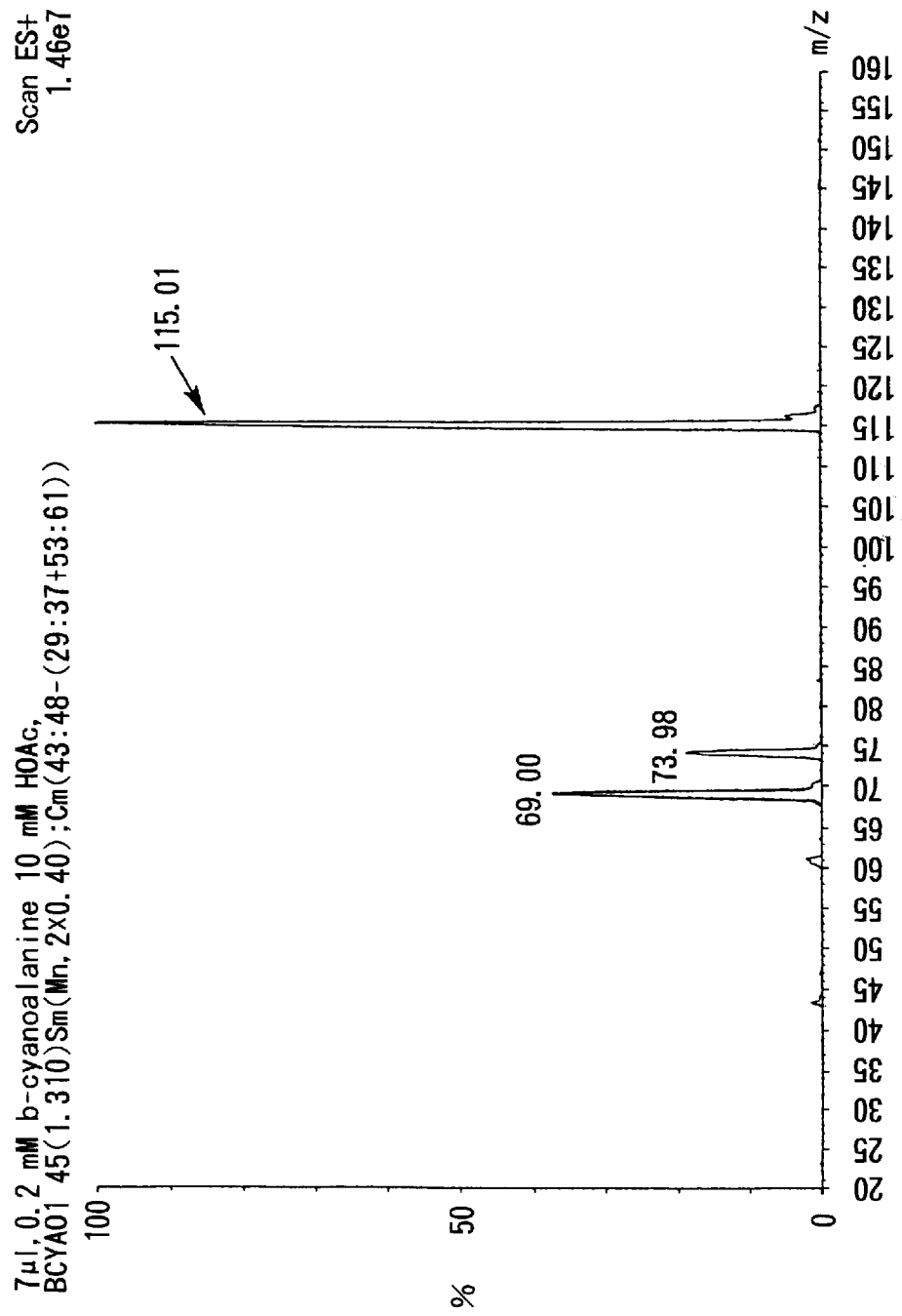
FIG. 3 is the mass-analysis spectrum for the reaction product of Example 2.

FIG. 3 which illustrates a quantitative analysis spectrum permitted confirmation as well, together with the results shown in FIGS. 1 and 2, of the fact that the reaction product was β-cyano-L-alanine.

EXAMPLE 3

Reducing agents CoBr$_2$ and NaBH$_4$ were added to the labelled β-cyano-L-alanine obtained in Example 2 for reduction. Then, after filtration (0.2 μm), 6M hydrochloric acid in an amount of 500 μl was added and the mixture was filtered through a 0.2 μm filter to remove protein and collect an enzyme, which was then purified with HPLC.

The product was analyzed under the following HPLC conditions:

Column: Beckman CX (4.6×250 mm);
Eluent: 10 mM Potassium phosphate buffer (pH: 4.6);
Flowrate: 2 ml/min.;
Detection: UV 220 nm and Radiodetector;
Temperature: Room temperature; and
Injection volume: 10–40 μl.

Figure 4:
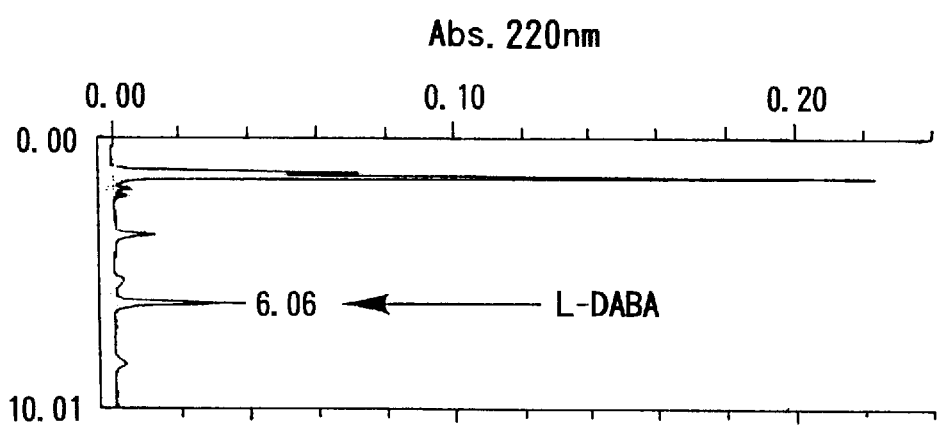
FIG. 4 is the result of HPLC analysis showing that the reaction product of Example 3 is DABA.
Figure 5:
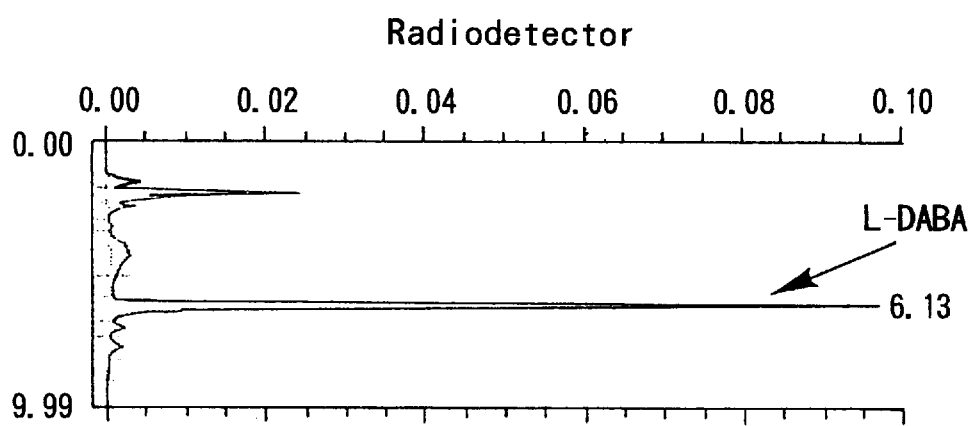
FIG. 5 is the result of HPLC analysis showing that the reaction product of Example 3 is DABA labelled with $^{11}C$.

The results of analysis using UV 220 nm and Radiodetector are shown in FIGS. 4 and 5. These results show that the reaction product was L-2,4-diaminobutyric acid (L-DABA) labelled with $^{11}$C. This compound had a radiochemical purity of at least 96% and a radiochemical yield within a range of from 30 to 40%.

Figure 6A:
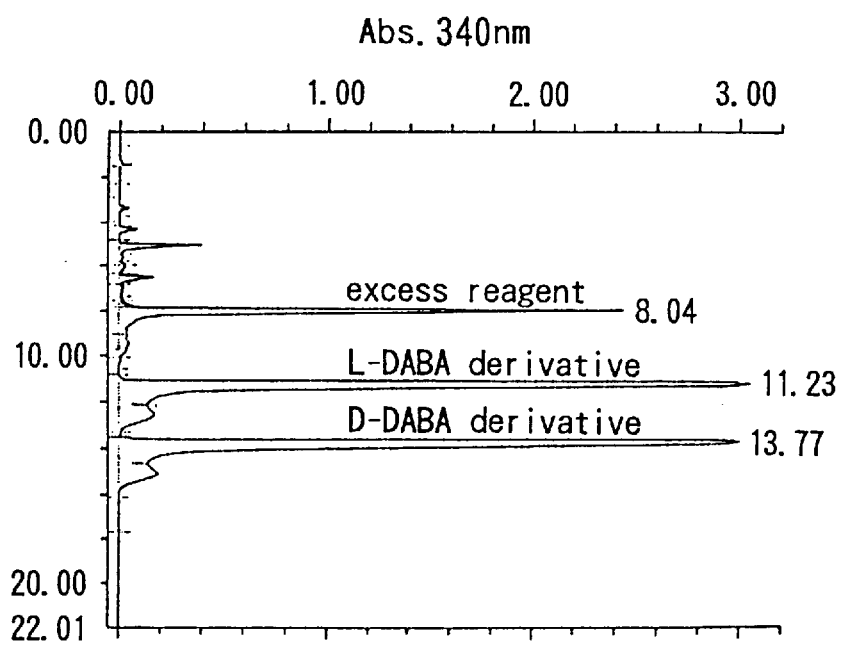
FIGS. 6(a)–6(b) are the result of HPLC analysis showing that the $^{11}C$-labelled DABA of Example 3 is L-form.
Figure 6B:
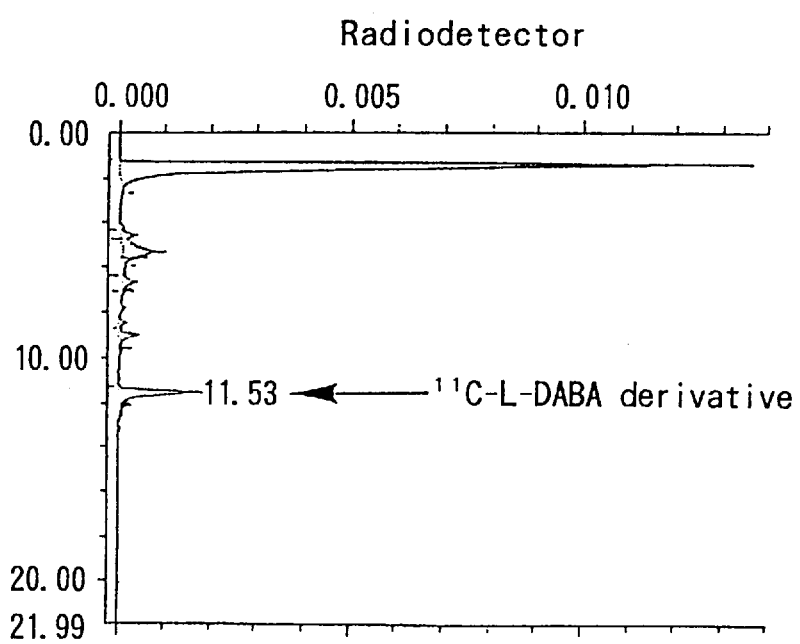

FIG. 6 illustrates values of analysis based on UV 340 nm and Radiodetector carried out for identification of L-DABA and D-DABA. It is thus proved that the DABA enzymatically synthesized in the present invention is of the L-form. The chart (a) of FIG. 6 shows a racemi authentic sample of DABA as converted into a derivative to perform HPLC analysis. D and L-forms were converted into derivatives with reference to the method of Marfey P. (Carlsberg Res. Commun. 49,591, 1984).

The chart (b) of FIG. 6 also demonstrates that the enzymatically synthesized DABA is of L-form.

13

EXAMPLE 4

Biological applicability of the $^{11}$C-labelled L-DABA obtained in Example 3 was evaluated. The relationship between concentration of the L-DABA added to culture medium of rat glioma and uptake of radioactivity into the glioma cells in a given duration was investigated in a medium having an amino acid content close to the biological one, and for control, in a physiological saline buffered with phosphoric acid.

Figure 7:
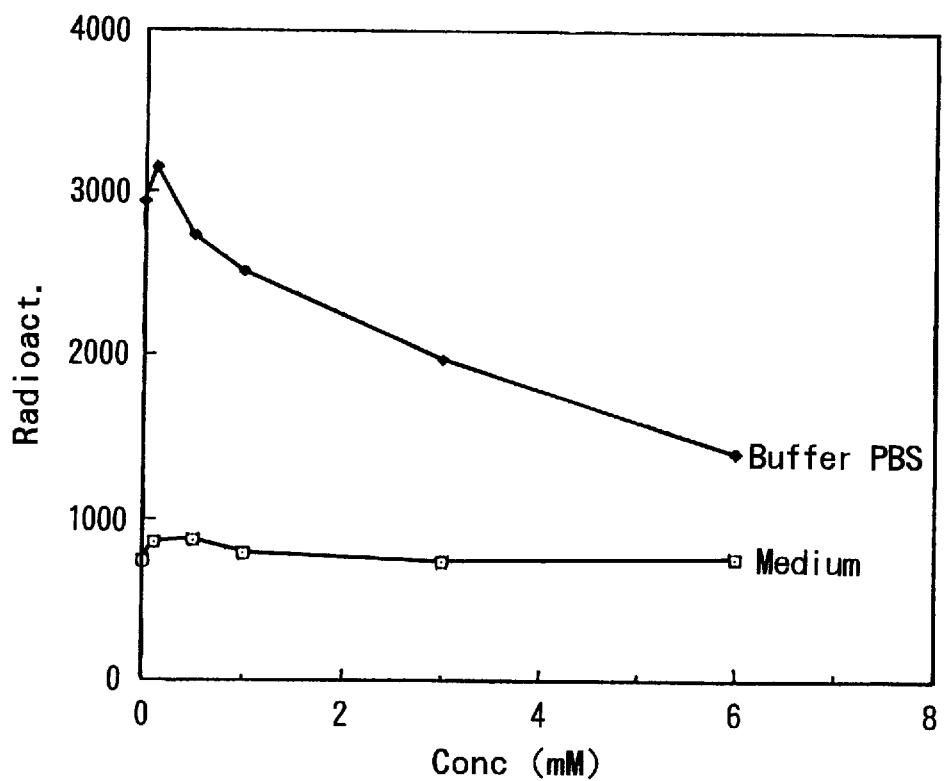
FIG. 7 shows the uptake of $^{11}C$-labelled DABA of Example 3 into gliomacyte.

The results are shown in FIG. 7. From the results, it is known that the uptake of $^{11}$C-labelled L-DABA was dependent on the concentration of it in culture medium, and has properties as a satisfactory labelling substance applicable to biological bodies.

EXAMPLE 5

A thermostable γ-cyano-α-aminobutyric acid synthase was prepared as follows.

Dry bouillon medium NISSUI for general bacteria (made by Nissui Seiyaku Company) was poured into four test tubes (2.2 cm diameter×19.5 cm length), sterilized at 120° C. for 20 minutes and cooled. Then, *Bacillus stearothermophilus* CN3 strain was inoculated to the cooled medium by an amount of one platinum dose. A basic culture medium was prepared by shake-culturing the inoculated medium at 58° C. for 18 hours. A medium (pH: 7.2) comprising 1% soluble starch, 0.5% yeast extract, 0.05% $MgSO_4$ $7H_2O$, 0.1% $K_2HPO_4$, 0.001% $FeSO_4$ $7H_2O$, and 0.1% L-glutamine was poured into four culturing flasks having a volume of 2 l each in an amount of 400 ml. After sterilization at 120° C. for 20 minutes and cooling, the above-mentioned basic culture medium in an amount of 16 ml (in the four test tubes) was inoculated by an amount of 4 ml to each of the flasks, and the inoculated medium was shake-cultured at 58° C. for 18 hours to prepare a preculture medium. Then, a medium prepared by adding an antifoaming agent ADEKANOL LG126 (made by Asahi Denka Company) in an amount of 0.01% (W/V) to a medium having the same composition as above. The resultant medium in an amount of 160 l was placed in a jar fermenter having a volume of 200 l. After sterilization at 120° C. for 20 minutes and cooling, the above-mentioned preculture medium in an amount of 1.6 l was inoculated and culturing was carried out at 58° C. for 18 hours under conditions including a flowrate of aeration of 160 l/minute and a stirring velocity of 200 rpm. After the completion of culture, bacteria were collected through sharpless.

The resultant bacteria in an amount of 660 g was suspended in a potassium phosphate buffer solution (20 mM, pH: 7.5, containing 0.1 mM dithiothreitol) so as to achieve a total amount of 2.5 l, and the suspension was milled in "Dyno Mill" (made by WAB Company). The milled solution was subjected to centrifugal separation to remove bacterial residue, and a cell-free extract in an amount of 2,799 ml was obtained. The thus obtained cell-free extract was held at 60° C. for 30 minutes, and produced precipitate was removed by centrifugal separation to give a supernatant.

Ammonium sulfate was added to this supernatant so as to achieve 40% saturation, and the saturated supernatant was held for a night. The precipitate was removed by centrifugal separation. Ammonium sulfate was added again to the resultant supernatant to achieve 90% saturation, and the mixture was held for a night, thus resulting in a precipitate. The precipitate was dissolved in a 20 mM potassium phosphate buffer solution (pH: 7.5) containing 0.1 mM dithiothreitol and 0.01 mM pyridoxal phosphate, and desalted by this buffer solution with the use of a dialysis membrane. The desalted solution was passed through a previously equilibrated DEAE-cellurofine A-500 column (8 cm diameter×22 cm length) for adsorption of an enzyme. After washing with a 100 mM potassium phosphate buffer solution (pH: 7.5) containing 0.1 mM dithiothreitol and 0.01 mM pyridoxal phosphate, the enzyme was eluted by the gradient elution method from this buffer solution to a 100 mM potassium phosphate buffer solution (pH: 7.5) containing 0.1 mM dithiothreitol, 0.01 mM pyridoxal phosphate and 0.4M KCL, thus collecting an active fraction.

Then, ammonium sulfate was added to the resultant active fraction to achieve 60% saturation, and after holding for a night, produced precipitate was removed through centrifugal separation. Ammonium sulfate was added again to the supernatant thus obtained to achieve 75% saturation, which was held for a night, and a precipitate was obtained through centrifugal separation. This precipitate was dissolved in 30% saturated ammonium sulfate and 20 mM potassium phosphate buffer solution (pH: 7.5) containing 0.1 mM dithiothreitol and 0.01 mM pyridoxal phosphate, and the resultant solution was passed through a Phenyl-Toyopal 650S column (2.5 cm diameter×8.5 cm length) previously equilibrated by the above-mentioned buffer solution to adsorb the enzyme. After washing with this buffer solution, the enzyme was eluted from this buffer solution to a 20 mM potassium phosphate buffer solution (pH: 7.5) containing 0.1 mM dithiothreitol and 0.01 mM pyridoxal phosphate by the gradient elution method and an active fraction was collected.

Ammonium sulfate was added to the thus collected active fraction so as to achieve 80% saturation, and after holding for a night, a precipitate was obtained by centrifugal separation. This precipitate was dissolved in a 50 mM sodium phosphate buffer solution (pH: 7.5) containing 0.1 mM dithiothreitol and 0.2M NaCl. The solution was then applied to a Sephacryl S-200HR column (2.0 cm diameter×106 cm length) previously equilibrated with the above-mentioned buffer solution, and an active fraction was collected by eluting enzyme with this buffer solution.

Ammonium sulfate was added to the collected active fraction so as to achieve 80% saturation, and after holding for a night, a precipitate was obtained through centrifugal separation. This precipitate was dissolved in a 100 mM sodium phosphate buffer solution (pH: 7.0) containing 0.2M NaCl, and the solution was poured at a flow rate of 0.7 ml/minute as a mobile phase into a TSK gel-G3000SW column (0.75 cm diameter×60 cm length) for HPLC to take out the active fraction. The resultant enzyme was electrophoretically homogeneous, having a specific activity of 147 U/mg.

Total activity, total protein, specific activity, purifying magnifications and yield of the enzyme obtained in the above-mentioned extraction and purifying steps were as shown in Table 4. Enzyme activity was measured by incubating a reaction solution (total amount: 200 μl) comprising 10 μl 1M potassium phosphate buffer solution (pH: 7.5) (ultimate concentration: 50 mM), 100 μl 10 mM O-acetyl-L-homoserine (ultimate concentration: 5 mM), 20 μl 100 mM potassium cyanide (ultimate concentration: 10 mM), 20 μl 0.8 mM pyridoxal phosphate (ultimate concentration: 0.08 mM), and 50 μl enzyme solution at 45° C. for 10 minutes, discontinuing the reaction by placing the mixture in boiling water bath for two minutes, then subjecting a supernatant centrifugally separated at 10,000 rpm for five minutes to HPLC, and measuring γ-cyano-α-aminobutyric acid produced through the enzymatic reaction.

As the unit for enzyme activity, the enzyme activity of producing 1 μmol γ-cyano-α-aminobutyric acid in a minute under the following conditions was defined as a unit. The conditions for HPLC was:

Column: Inertsil ODS-2 (4.6 mm inside diameter×250 mm; made by G.L. Science Company), and Eluent: 20 mM sodium phosphate buffer solution (pH 6.8)/acetonitrile (85:15).

TABLE 4

| Step | Total activity (units) | Total protein (mg) | Specific activity (units/mg) | Fold | Yield (%) |
|---|---|---|---|---|---|
| 1. Cell-free extract | 1040 | 38100 | 0.0272 | 1 | 100 |
| 2. Heat treatment | 1460 | 30500 | 0.0479 | 1.76 | 140 |
| 3. $(NH_4)_2SO_4$ 40–90% | 1980 | 20700 | 0.0957 | 3.52 | 190 |
| 4. DEAE-Cellurofine A-500 | 1470 | 3970 | 0.370 | 13.6 | 141 |
| 5. $(NH_4)_2SO_4$ 60–75% | 1710 | 821 | 2.08 | 76.5 | 164 |
| 6. Phenyl Toyopal 650S | 932 | 64.4 | 14.5 | 533 | 89.6 |
| 7. Sephacryl S-200HR | 479 | 27.9 | 17.2 | 632 | 46.1 |
| 8. TSK gel-G3000SW | 58.1 | 0.395 | 147 | 5404 | 5.59 |

(from 160 l of culture medium)

Further, for the γ-cyano-α-amino-butyric acid synthase obtained, tests were carried out on optimum pH, stable pH, optimum temperature, thermo-stability and molecular weight.

Figure 8:
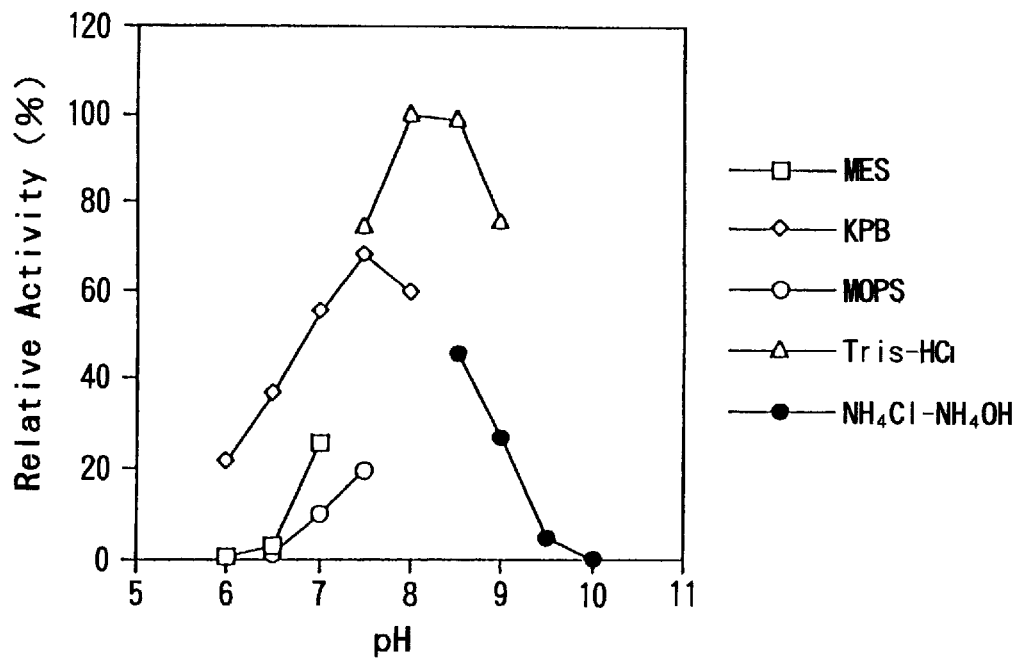
FIG. 8 illustrates an optimum pH of thermostable γ-cyano-α-aminobutyric acid synthase.

1. Optimum pH:

Enzyme activity was measured by replacing the buffer of reaction solution for measuring activity in the enzyme activity measuring method described above with MES (pH: 6.0 to 7.0), KPB (pH: 6.0 to 8.0), MOPS (pH: 6.5 to 7.5), Tris-HCl (pH: 7.5 to 9.0), and $NH_4Cl$—$NH_4OH$ (pH: 8.5 to 10.0). The results are as shown in FIG. 8: the optimum pH of this γ-cyano-α-aminobutyric acid synthase was found to be within a range of from 7.5 to 8.5.

Figure 9:
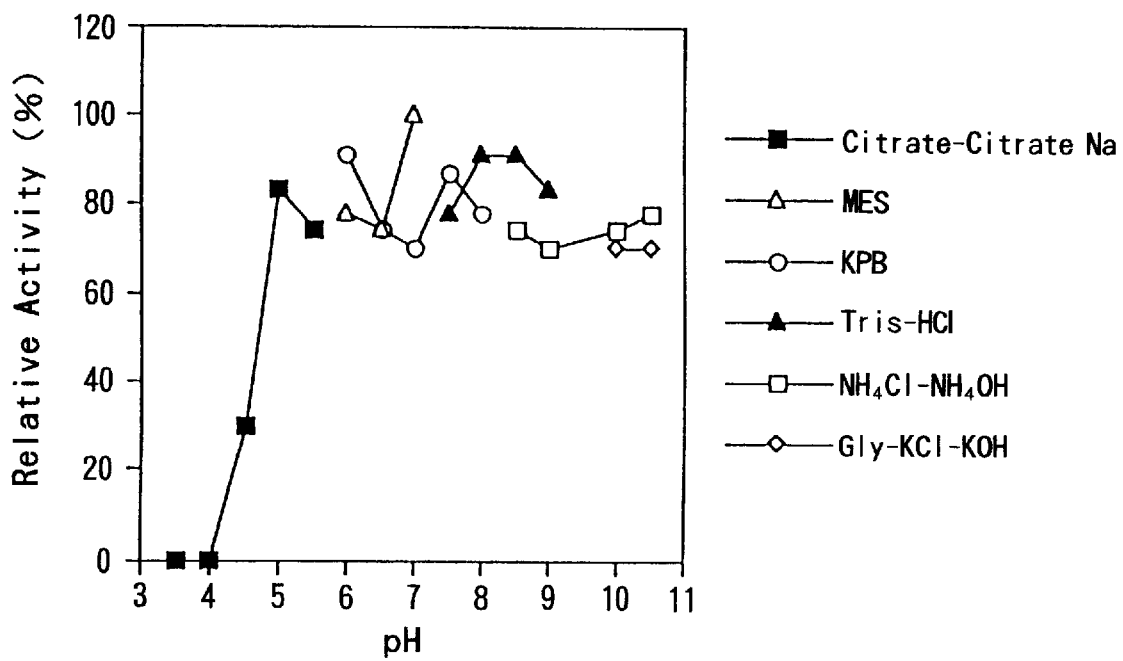
FIG. 9 shows a pH stability thereof.

2. Stable pH:

The γ-cyano-α-aminobutyric acid synthase was dissolved in various 20 mM concentration buffer solutions, i.e., citric acid/sodium citrate (pH: 3.5 to 5.5), MES (pH: 6.0 to 7.0), KPB (pH: 6.0 to 8.0), Tris-HCl (pH: 7.5 to 9.0), $NH_4Cl$—$NH_4OH$ (pH: 8.5 to 10.0), and glycine/KCl-KOH (pH: 10.0 to 10.5), respectively, and residual activity after holding at 60° C. for 30 minutes was measured. The results are as shown in FIG. 9: the stable pH for this γ-cyano-α-aminobutyric acid synthase was found to be within a range of from 6.0 to 10.5.

Figure 10:
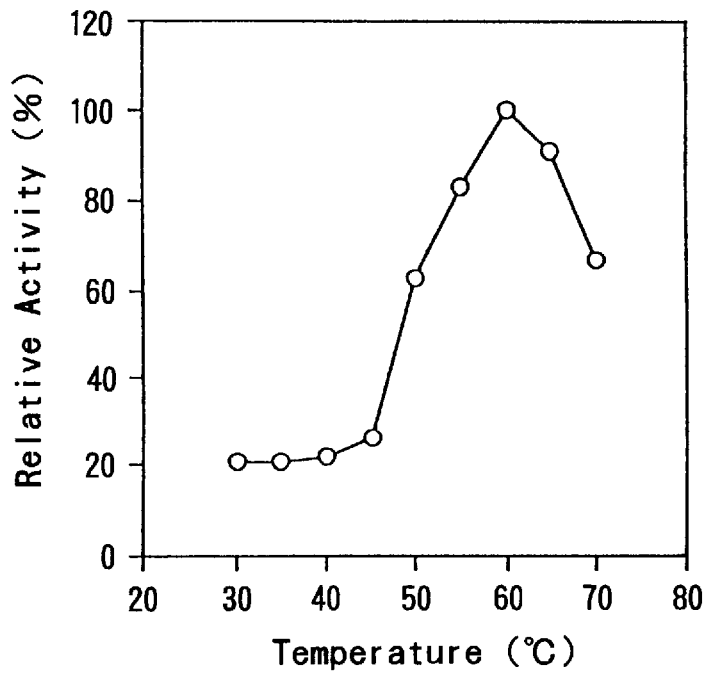
FIG. 10 shows an optimum temperature thereof.

3. Optimum temperature:

The γ-cyano-α-aminobutyric acid synthase was dissolved in a 20 mM potassium phosphate buffer solution (pH: 7.5), and enzyme activity was measured within a temperature range of from 30° C. to 70° C. by the enzyme activity measuring method described above. The results are as shown in FIG. 10: the optimum temperature for this γ-cyano-α-aminobutyric acid synthase was found to be within a range of from 55° to 65° C.

Figure 11:
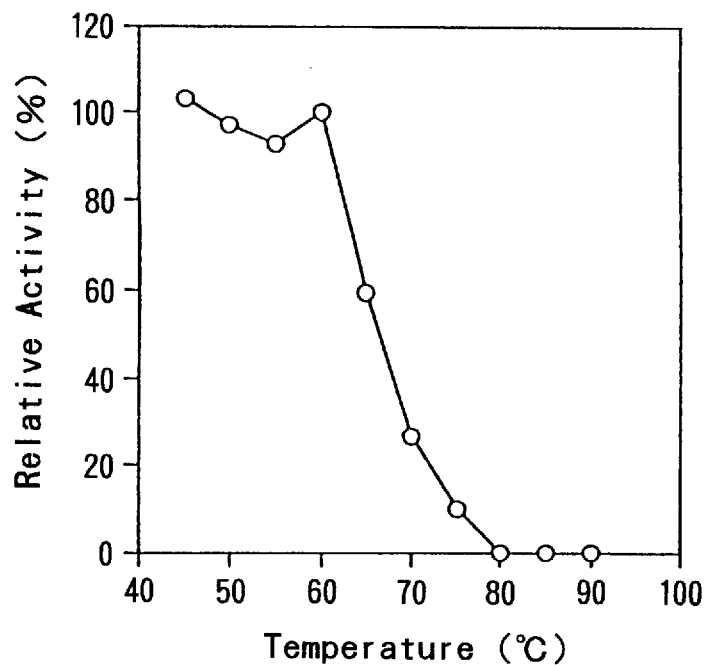
FIG. 11 shows temperature stability thereof.

4. Thermostability:

The γ-cyano-α-aminobutyric acid synthase was dissolved in a 20 mM potassium phosphate buffer solution (pH: 7.5), and after holding at each of various temperatures of from 45° C. to 90° C. for 30 minutes, residual activity was measured. The results are as shown in FIG. 11: the γ-cyano-α-aminobutyric acid synthase was found to have a very high thermostability, and to be stable at temperatures up to 65° C.

Figure 12:
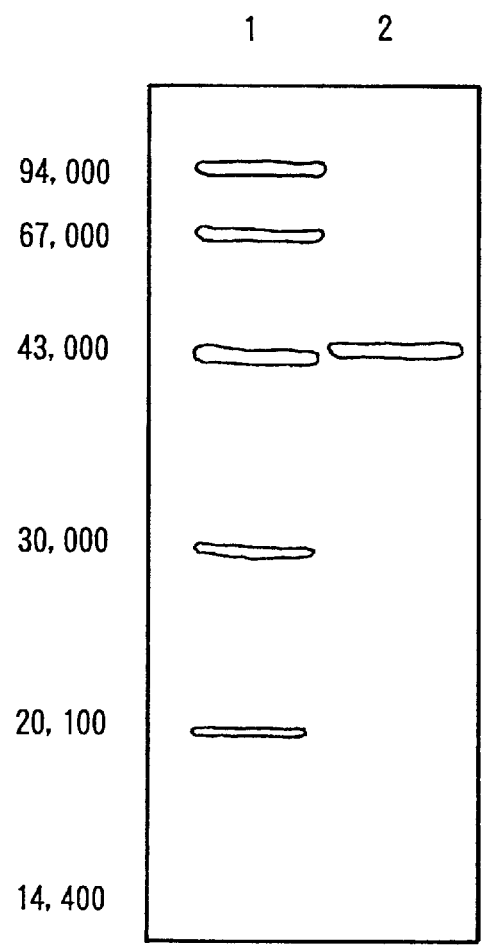
FIG. 12 illustrates a subunit molecular weight of thermostable γ-cyano-α-aminobutyric acid synthase by SDS-PAGE.
Figure 13:
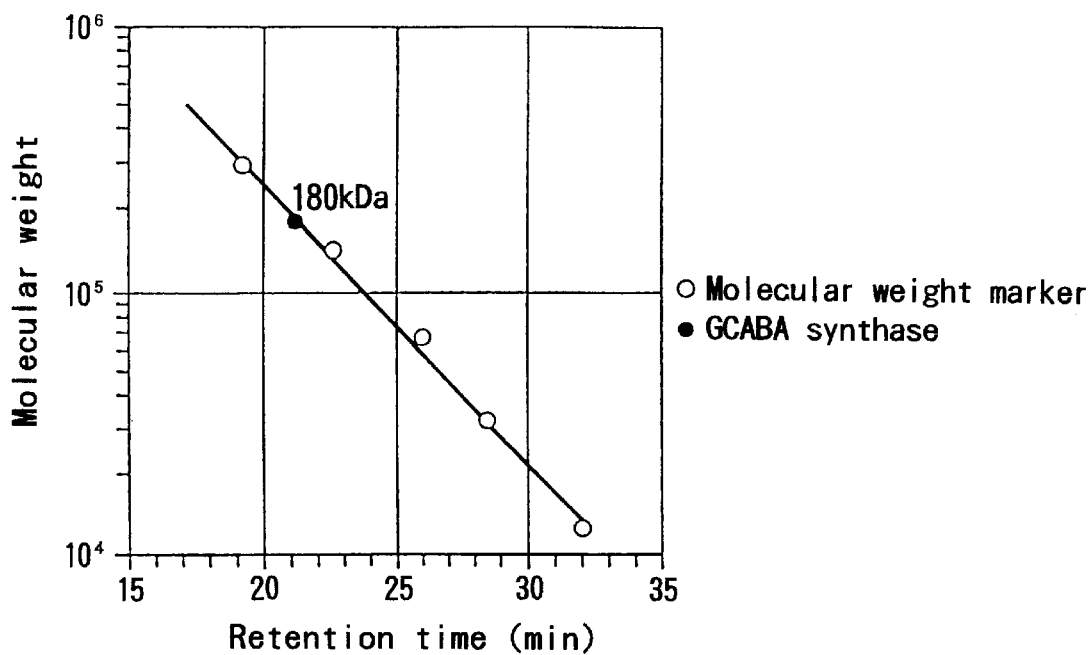
FIG. 13 shows a graph of molecular weights of the enzyme by gel filtration.

5. Molecular weight:

The molecular weight of the thermostable γ-cyano-α-aminobutyric acid synthase was measured by gel filtration and SDS-PAGE. The results are as shown in FIGS. 12 and 13: the molecular weight was confirmed to be about 43 kDa (FIG. 12) as measured by the SDS-PAGE, and about 180 kDa (FIG. 13) as measured by gel filtration.

Figure 14:
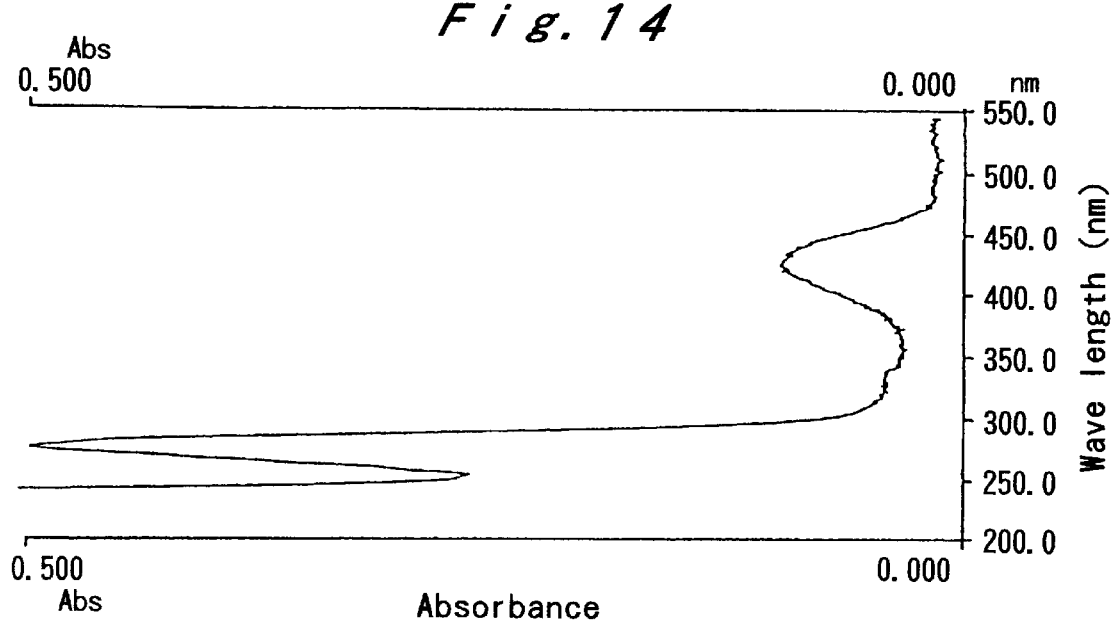
FIG. 14 shows the result of absorption spectral analysis of purified thermostable γ-cyano-α-aminobutyric acid synthase.

6. Absorption spectrum:

The thermostable γ-cyano-α-aminobutyric acid synthase was dissolved in a 20 mM potassium phosphate (pH: 7.5) containing 0.1 mM dithiothreitol and 0.01 mM pyridoxal phosphate, and absorption spectrum was measured on this solution by means of a U-3200 type spectrophotometer (made by Hitachi Ltd.). The results are as shown in FIG. 14: for the thermostable γ-cyano-α-aminobutyric acid synthase of the present invention, absorption was observed within a range of from 410 to 440 nm, which is intrinsic to an enzyme utilizing pyridoxal phosphate as coenzyme.

EXAMPLE 6

$H^{11}CN$ was manufactured by reducing $^{11}C$ containing positron nuclide $^{11}C$ prepared in cyclotron into $^{11}CH_4$ at 400° C. in the presence of Ni in a mixed atmosphere of $H_2$ and $N_2$, and contact reacting the resultant $^{11}CH_4$ with ammonia at a temperature of 1,000° C. in the presence of a platinum (Pt) catalyst. This process was based on a known method (Iwata et al. Appl. Radiat. 38, 97, 1987). Then, $H^{11}CN$ in the form of a mixed gas was passed through a 50% $H_2SO_4$ solution in an amount of 1.5 ml to remove residual ammonia, and after further removing ammonia by bringing same into contact with $P_2O_5$, $H^{11}CN$ was trapped with 50 mM KOH in an amount of 350 μl.

Then, 250 μl 200 mM $K_2HPO_4$, 10 μl 10 mM pyridoxal phosphate (PLP), 110 μl 25 mM O-acetyl-L-homoserine (OAHS) dissolved in 100 mM $K_2HPO_4$, and γ-cyano-α-aminobutyric acid synthase (GCAs) obtained in Example 5 were added to this trapped $H^{11}CN$, and the mixture was subjected to enzymatic reaction at 65° C. for 10 minutes.

The reaction solution was analyzed with UV 220 nm and a radiodetector by means of HPLC. This reaction product showed the same retention time as that of the standard γ-cyano-α-aminobutyric acid, and was confirmed to be labelled with positron nuclide $^{11}C$. The γ-cyano-α-aminobutyric acid synthesized by the enzymatic reaction had a radiochemical yield (corrected decay value) of 93.99%.

EXAMPLE 7

NaOH of 2.5M was added to a reaction solution containing the γ-cyano-α-aminobutyric acid of which cyano group carbon being labelled with positron nuclide $^{11}C$, as obtained in Example 6, and temperature of the mixture was raised to 135° C. After the lapse of 15 minutes, the reaction solution was mixed with 8 ml 50 mM $NaH_2PO_4$, and the resultant mixture was passed through an anion exchange resin (800 mg AGI-x8 200–400 mesh hydroxide form). After washing with 50 mM $NaH_2PO_4$ in an amount of 6 ml, the reaction product was eluted with 150 mM $NaH_2PO_4$ (pH adjusted to 2.8 with phosphoric acid), and the elute was received in a receptacle containing 150 μl 8.5% phosphoric acid. The contents were passed through a sterilized filter having a pore diameter of 0.2 μm for collection in bial. The product was germ-free, and no exothermic substance was detected.

Figure 15A:
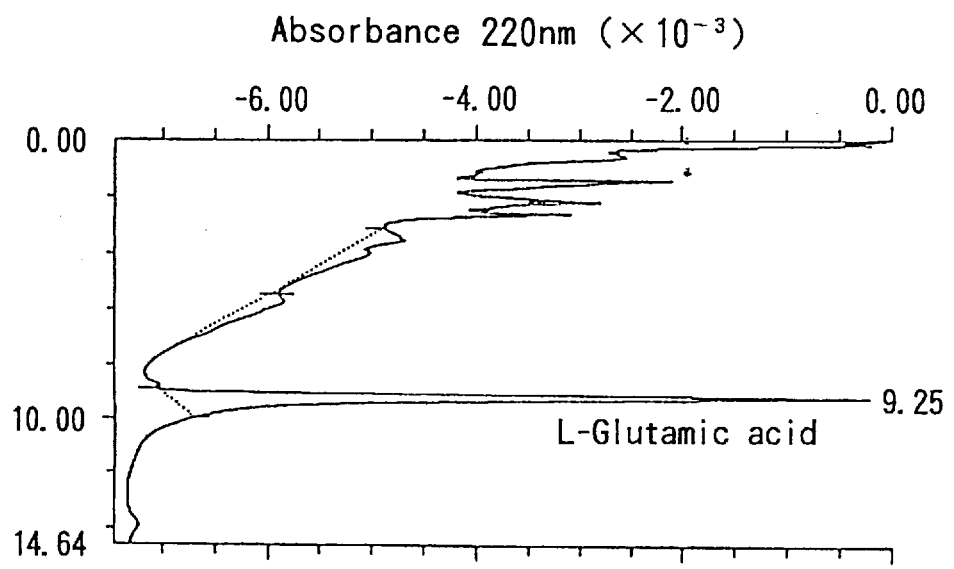
FIGS. 15(a)–15(b) are the result of HPLC analysis showing that the reaction product of Example 7 is L-glutamic acid.
Figure 15B:
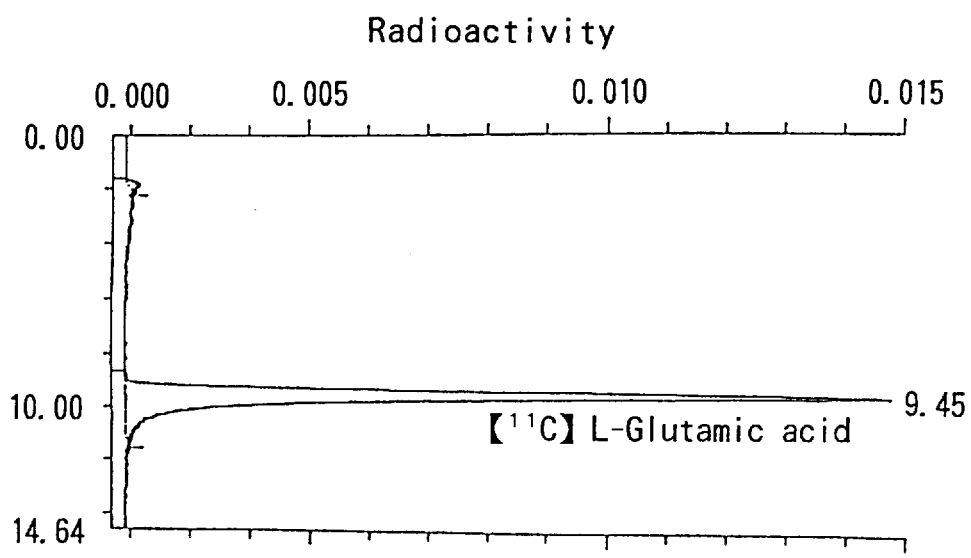
Figure 16A:
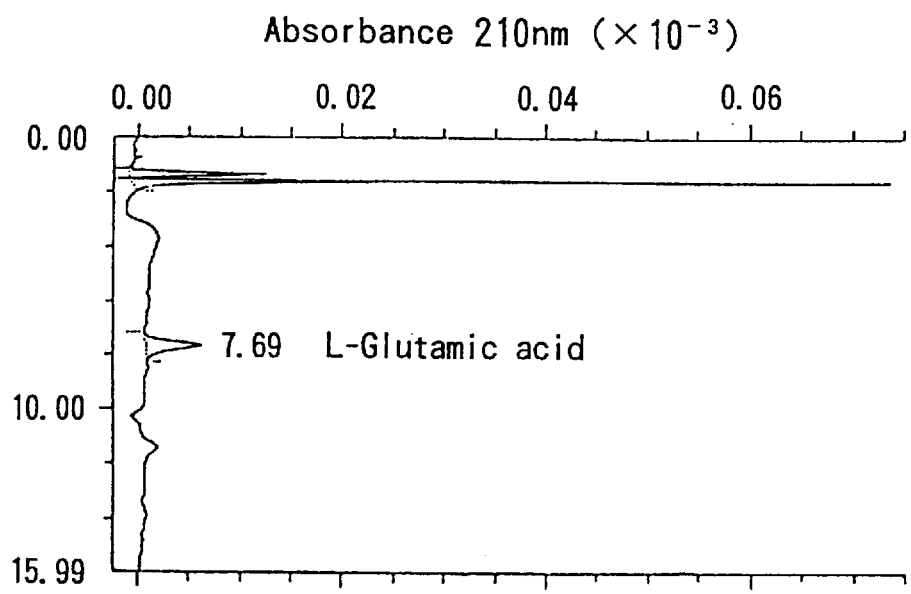
FIGS. 16(a)–16(b) are the result of HPLC analysis showing that the reaction product of Example 7 is L-glutamic acid labelled with $^{11}C$.
Figure 16B:
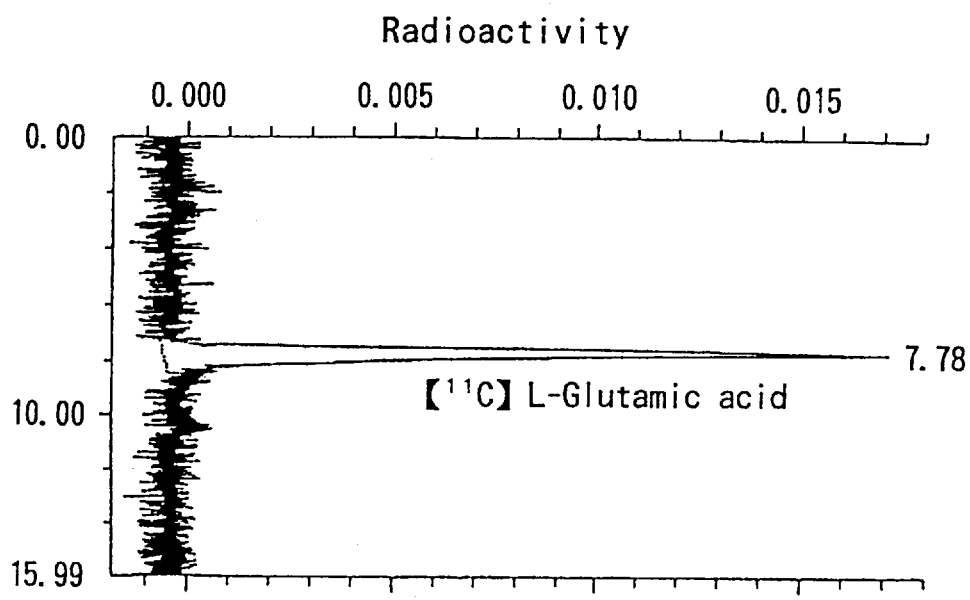

FIGS. 15 and 16 illustrate the results of HPLC analysis carried out by admixing standard glutamic acid to the above-mentioned reaction product. The analysis shown in FIGS. 15(a) and (b) was carried out under the following conditions:

Column: $LC-NH_2$ 4.6×250 mm 5 μm;
Eluent: 10 mM $KH_2PO_4/CH_3CN$, linear gradient 15/85 to 80/20, 0–7 min;
Flow rate: 1 ml/min;
Detection: UV 220 nm and Radiodetector; and
Temperature: Room temperature.

The conditions for analysis of FIGS. 16(a) and (b) were as follows:

Column: Beckman CX 4.6×250 mm;
Eluent: 10 mM $KH_2PO_4/CH_3CN$ (95/5);
Flow rate: 2 ml/min;
Detection: UV 210 nm and Radiodetctor; and
Temperature: Room temperature.

As is clear from these results of analysis, peaks were in agreement between the labelled compound and the standard glutamic acid under different conditions using two different columns. It was thus confirmed that the above-mentioned reaction product was $^{11}C$-labelled glutamic acid.

The resultant $^{11}C$-labelled glutamic acid had a radiochemical yield (decay corrected value) of about 50% and a radiochemical purity of at least 95%.

FIG. 17 shows the results of measurement of optical purity of the $^{11}C$-labelled glutamic acid, in which (a) is a chart of HPLC in the case where a racemi standard glutamic acid is converted into a derivative, and (b) gives the result of analysis carried out by similarly converting the enzymatically synthesized $^{11}C$-labelled glutamic acid into a derivative. The analytic conditions were as follows:

Column: Beckman ODS (C-18) 4.6×250 mm 5 μm;
Eluent: 0.05M ammonium formate, (pH: 3.5)/Methanol, linear gradient 55/45 to 40/60, 0–6 min.;
Flow rate: 2 ml/min.;
Detection: UV 340 nm and Radiodetector; and
Temperature: Room temperature.

It was confirmed from these results that the $^{11}C$-labelled glutamic acid was of the L-form. The method for conversion into derivative of glutamic acid was in accordance with Marfey's et al (Determination of enantiomenic excess: Determination of D-amino acid. II. Use of a bifunctional reagent, 1,5-difluoro-2,4-dinitrobenzene, Marfey P. Carlsberg Res. Commun., 49, 591, 1984).

What is claimed is:

1. A labelled compound, which is β-cyano-L-alanine, a salt thereof or a derivative thereof having protecting group, of which cyano group carbon is labelled with positron nuclide $^{11}C$.

* * * * *